US008882673B2

(12) United States Patent
Guzman

(10) Patent No.: US 8,882,673 B2
(45) Date of Patent: Nov. 11, 2014

(54) CONTINUOUS TRANSVERSUS ABDOMINIS PLANE BLOCK

(75) Inventor: Michael F. Guzman, Fortville, IN (US)

(73) Assignee: I-Flow Corporation, Lake Forest, CA (US)

(*) Notice: Subject to any disclaimer, the term of this patent is extended or adjusted under 35 U.S.C. 154(b) by 308 days.

(21) Appl. No.: 13/025,448

(22) Filed: Feb. 11, 2011

(65) Prior Publication Data

US 2011/0201930 A1  Aug. 18, 2011

Related U.S. Application Data

(60) Provisional application No. 61/303,766, filed on Feb. 12, 2010.

(51) Int. Cl.
A61B 8/00 (2006.01)
A61B 8/08 (2006.01)

(52) U.S. Cl.
CPC .................................. A61B 8/0841 (2013.01)
USPC .............. 600/439; 600/585; 604/21; 604/528

(58) Field of Classification Search
None
See application file for complete search history.

(56) References Cited

U.S. PATENT DOCUMENTS 5,562,695 A * 10/1996 Obenchain .................... 606/185
5,730,754 A * 3/1998 Obenchain .................... 606/185
5,916,172 A * 6/1999 Hodges et al. ................. 600/546
6,101,412 A * 8/2000 Duhaylongsod .................. 607/2
6,185,451 B1 * 2/2001 Richardson et al. ........... 600/546
6,347,247 B1 * 2/2002 Dev et al. .......................... 607/2
6,491,647 B1 * 12/2002 Bridger et al. ................. 600/585
6,496,561 B1 * 12/2002 Meyer et al. ..................... 378/65
6,716,412 B2 * 4/2004 Unger .......................... 424/9.52
6,832,984 B2 * 12/2004 Stelzer et al. .................. 600/106
6,865,416 B2 * 3/2005 Dev et al. .......................... 607/2
6,994,700 B2 * 2/2006 Elkins et al. ................... 604/528
7,104,981 B2 * 9/2006 Elkins et al. ................... 604/528
7,149,574 B2 * 12/2006 Yun et al. .......................... 607/2
7,239,912 B2 * 7/2007 Dobak, III ........................ 607/2
7,493,154 B2 * 2/2009 Bonner et al. ................. 600/424
2004/0087877 A1 * 5/2004 Besz et al. ..................... 600/585

(Continued)

OTHER PUBLICATIONS

Barrington et al, "Spread of injectate after ultrasound-guided subcostal transversus abdominis plane block: a cadaveric study", Anaesthesia, 2009, 64, pp. 745-750.*

(Continued)

Primary Examiner — Nicholas Evoy
(74) Attorney, Agent, or Firm — Dority & Manning, P.A.

(57) ABSTRACT

A procedure and kit are provided for performing an ultrasound-guided transversus abdominis plane (TAP) procedure. The patient's abdomen is scanned with an ultrasound probe to identify and mark the external oblique, internal oblique, and TAP. An introducer sheath is placed over a fluid delivery needle such that the distal end of the needle extends beyond the distal end of the sheath, the needle having echogenic properties for ultrasound imaging. The needle and sheath are ultrasonically guided into the TAP. A local anesthetic or saline/anesthetic combination is injected through the needle to create a liquid pool in the TAP. The needle is removed from the sheath while maintaining the sheath within the TAP and a catheter is subsequently advanced through the sheath and into the pooled liquid in the TAP. The sheath is withdrawn while maintaining the catheter located within the TAP. A catheter is connected to a source of local anesthetic for providing a defined volume of anesthetic to the catheter site at a controlled delivery rate.

7 Claims, 6 Drawing Sheets

(56) References Cited

U.S. PATENT DOCUMENTS

| | | | |
|---|---|---|---|
| 2005/0107829 A1* | 5/2005 | Edwards et al. | 607/2 |
| 2005/0171575 A1* | 8/2005 | Dev et al. | 607/2 |
| 2006/0015131 A1* | 1/2006 | Kierce et al. | 606/191 |
| 2006/0025797 A1* | 2/2006 | Lock et al. | 606/191 |
| 2006/0089633 A1* | 4/2006 | Bleich et al. | 606/32 |
| 2006/0095059 A1* | 5/2006 | Bleich et al. | 606/170 |
| 2006/0206155 A1* | 9/2006 | Ben-David et al. | 607/9 |
| 2007/0021686 A1* | 1/2007 | Gellman et al. | 600/585 |
| 2007/0060954 A1* | 3/2007 | Cameron et al. | 607/2 |
| 2007/0156179 A1* | 7/2007 | Karashurov | 607/2 |
| 2007/0219596 A1* | 9/2007 | Dobak, III | 607/46 |
| 2007/0225768 A1* | 9/2007 | Dobak, III | 607/2 |
| 2008/0132926 A1* | 6/2008 | Eichmann et al. | 606/167 |
| 2008/0275458 A1* | 11/2008 | Bleich et al. | 606/103 |
| 2009/0005774 A1 | 1/2009 | Fernald | |
| 2009/0048537 A1* | 2/2009 | Lydon et al. | 600/585 |
| 2012/0059308 A1* | 3/2012 | Hsu et al. | 604/21 |

OTHER PUBLICATIONS

Belavy et al, "Ultrasound-guided transversus abdominis plane block for analgesia after Caesarean delivery", British Journal of Anaesthesia 103(5): 726-30 (2009).*

Mukhtar, "Transversus Abdominis Plane (TAP) Block", The Journal of New York School of Regional Anesthesia, 2006.*

Mukhtar, "Ultrasound-guided transversus abdominis plane block", Correspondance, British Journal of Anaesthsia.*

Niraj et al, "Analgesic efficacy of ultrasound-guided transversus abdominis plane block in patients undergoing open appendicectomy", British Journal of Anaesthesia, 103(4): 601-5 (2009).*

O'Connor, "Subcostal transversus abdominis plane block", Anaesthesia, 2010, 65, pp. 82-93.*

Tran et al, "Determination of spread of injectate after ultrasound-guided transversus abdominis plane block: a cadaveric study", British Journal of Anaesthsia 102(1): 123-7 (2009).*

Transversus Abdominis Plane (TAP) Block, New York School of Regional Anesthesia, 2009, vol. 12.

Ultrasound-guided Subcostal Transversus Abdominis Plane Block, International Journal of Ultrasound and Applied Technologies in Perioperative Care, Jan.-Apr. 2010.

Redefining Recovery, The On-Q Tunneling System—Taking Effective Pain Relief a Step Beyond.

Ultrasound-Guided Transversus Abdominis Plane Catheters and Ambulatory Perineural Infusions for Outpatient Inguinal Hernia Repair, Reg. Anesth. Pain Med., Nov. 2010.

Product Description, On-Q Catheters & Introducers, I-Flow Corporation.

Transversus Abdominis Plane (TAP) Block, Ultrasound for Regional Anesthesia, 2008.

Product Description, Contiplex and Stimuplex, B. Braun Melsungen, Germany.

Product Description, On-Q Post-Op Pain Relief System, I-Flow Corporation.

* cited by examiner

US 8,882,673 B2

CONTINUOUS TRANSVERSUS ABDOMINIS PLANE BLOCK

RELATED APPLICATIONS

The present application claims priority to U.S. Provisional Application Ser. No. 61/303,766 filed on Feb. 12, 2010, entitled "Continuous Transversus Abdominis Plane Block," which is incorporated herein by reference in its entirety for all purposes.

FIELD OF THE INVENTION

The present invention relates generally to the field of medical abdominal field blocks, and more particularly to methods and devices for performance of transversus abdominis plane (TAP) blocks.

BACKGROUND

The use of abdominal field blocks is well known for relieving pain experienced by patients after abdominal surgery. Conventional blocks, however, provide limited analgesic fields and, thus, multiple blind injections were usually required, with the success of such injections being unpredictable.

Transversus abdominis plane (TAP) blocks are a fairly recently developed single entry point procedure that accesses a number of the abdominal wall nerves, thereby providing a more widespread analgesic effect. The goal of a TAP block is to deposit local anesthetic in the plane between the internal oblique and transversus abdominis muscles to target the spinal nerves in this plane. The block is typically preformed blind, with the point of entry for the blind tap being the patient's triangle of Petit situated between the lower costal margin and the iliac crest and bound anteriorly by the external oblique muscle and posteriorly by the latissimus dorsi. The blind technique relies on the practitioner feeling double "pops" as the needle traverses the external oblique and internal oblique muscles.

Ultrasound-guided TAP blocks are gaining acceptance for providing better localization and injection of the local anesthetic with improved accuracy. With the ultrasound procedure, an ultrasound probe is placed in a plane essentially transverse to the lateral abdominal wall between the lower costal margin and the iliac crest. Ultrasonic imaging allows for a more accurate deposition of the local anesthetic in the correct neurovascular plane. Ultrasound-guided TAPS are indicated for essentially any lower abdominal surgery, including appendectomy, hernia repair, caesarean section, abdominal hysterectomy, and prostatectomy. Effectiveness has also been shown in laparoscopic surgery.

The present invention provides further advancements in the methodology and devices for ultrasound TAP procedures.

SUMMARY OF THE INVENTION

Objects and advantages of the invention will be set forth in part in the following description, or may be obvious from the description, or may be learned through practice of the invention.

In accordance with various aspects, a medical procedure is provided for performing an ultrasound-guided transversus abdominis plane (TAP) procedure. After prepping, the patient's abdomen is scanned with any suitable ultrasound probe, and the external oblique, internal oblique, and TAP are identified and marked. An introducer sheath is placed over a fluid delivery needle, such as an epidural needle, such that the distal end region of the needle extends beyond the distal end of the sheath. The needle is an echogenic device in that it is readily "detected" by the probe during ultrasound imaging. The ultrasound probe may be used throughout the procedure to relocate or confirm location of the TAP and various instruments within the TAP.

While ultrasonically imaging the site, the needle and sheath are advanced into the TAP and a liquid pool is created in the TAP by injecting a local anesthetic or saline/anesthetic combination through the needle. The needle is then removed from the sheath while maintaining the sheath within the TAP. A catheter is then slid through the sheath and into the pooled liquid in the TAP. Correct sheath placement may be verified by backflow of the liquid through the catheter as the catheter is extended beyond the sheath and into the liquid pool.

Once the catheter has been positioned, the sheath is withdrawn (e.g. by being slid proximally over the catheter) while maintaining the catheter stationary within the TAP. The catheter site may then be dressed and a reservoir of a local anesthetic connected to the proximal end of the catheter and configured for providing a defined volume of the anesthetic to the catheter site at a controlled delivery rate.

In a particular embodiment, the sheath may be advanced distally away from the needle and further into the liquid pool in the TAP prior to or in conjunction with removing the needle from the sheath. The sheath may be advanced until a slight resistance is felt by the practitioner (indicating that the sheath has reached the boundary of the liquid pool in the TAP).

The needle may be a Weiss epidural needle having fixed wings, which is connected to an extension set. A syringe may be used to inject the local anesthetic or saline/anesthetic through the extension set and needle to generate the liquid pool within the TAP. The extension set may be a simple tube that connects between the needle and syringe, or may include any manner of adapter, such as a 90-degree adapter, for enabling the procedure.

The distal portion of the needle that extends beyond the sheath is echogenic and thus readily visible during the ultrasound guidance of the needle and sheath into the TAP. It may, however, be desirable to also render the sheath echogenic to aid in the guidance procedure and to ultrasonically verify placement of the sheath after removal of the needle. In this regard, the sheath may contain any manner echogenic material, such as metal threads or flakes, formed with the sheath or subsequently added to the surface of the sheath. In another embodiment, the sheath may be rendered effectively echogenic by simply defining holes or perforations through the sheath such that that the metal needle is exposed through the perforations during the ultrasonically imaging. By detecting axial points or sections of the needle through the sheath, the location of the sheath is also verified.

In other aspects, the present invention encompasses any manner of medical procedure kit for performing an ultrasound-guided TAP procedure, as described above. In a particular embodiment, this kit may include a container, for example a tray having a sealed/removable covering. The components within the tray for performing the procedure may include a fluid delivery needle having a length and gauge for penetration into a patient's TAP. This needle may be, for example, a fixed-wing Weiss epidural needle. A sheath is included for operational configuration with the needle, as discussed above. The sheath has a size and length such that the needle slides into the sheath and extends distally beyond the distal end of the sheath. The sheath may include a proximal handle and a semi-rigid, echogenic section having a length so as to extend into the patient's TAP subsequent to removal of the needle from the sheath. The sheath may be rendered echogenic by inclusion of an echogenic material or a plurality of perforations defined along the axial length of the echogenic section.

An extension set may also be included in the kit, and may be variably configured with any manner of tubing, adapters, and the like. The extension set has a distal end that mates with the fluid delivery needle. A sheath is included having a size and length such that the needle slides into the sheath and extends distally beyond a distal end of the sheath.

A TAP catheter may be included in the kit having a size and length so as to slide through sheath and into the patient's TAP. The TAP catheter has a reservoir with a defined fill volume and delivery flow rate for controlled delivery of a local anesthetic to the catheter site.

The kit may include any manner or number of additional items for enabling the procedure. For example, the kit may include one or more vials of local anesthesia, saline, or a mix of anesthesia and saline, as well as a syringe that mates with a proximal end of the extension set to deliver the local anesthesia/saline through the needle to create the liquid pool in the TAP. Similarly, the kit may include any combination of drape, catheter site dressings, tape, and so forth.

BRIEF DESCRIPTION OF THE DRAWINGS

FIGS. 3A through 3H are depictions of various components and items that may be used in performance of an ultrasonically-guided TAP block procedure in accordance with aspects of the invention;

DETAILED DESCRIPTION OF THE INVENTION

Figure 1:
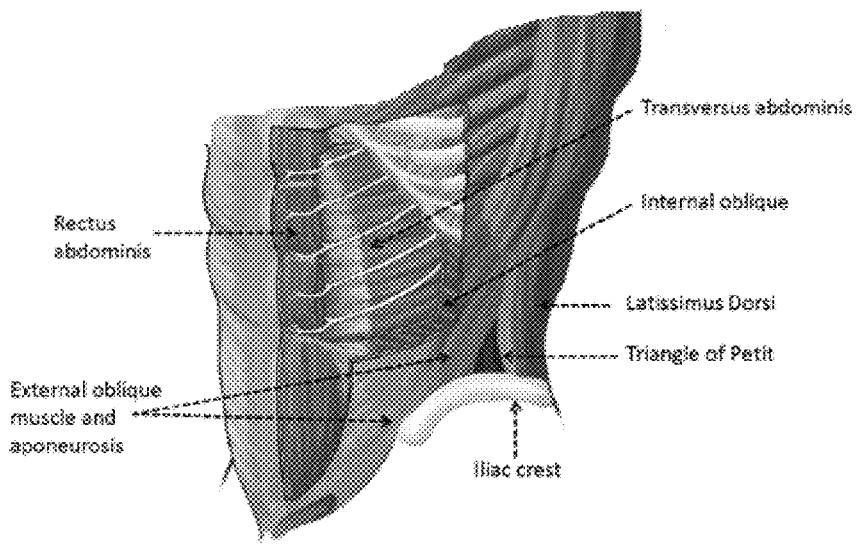
FIG. 1 is an illustration of regions of a human abdomen.

Reference will now be made in detail to one or more embodiments of the invention, examples of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

Figure 2:
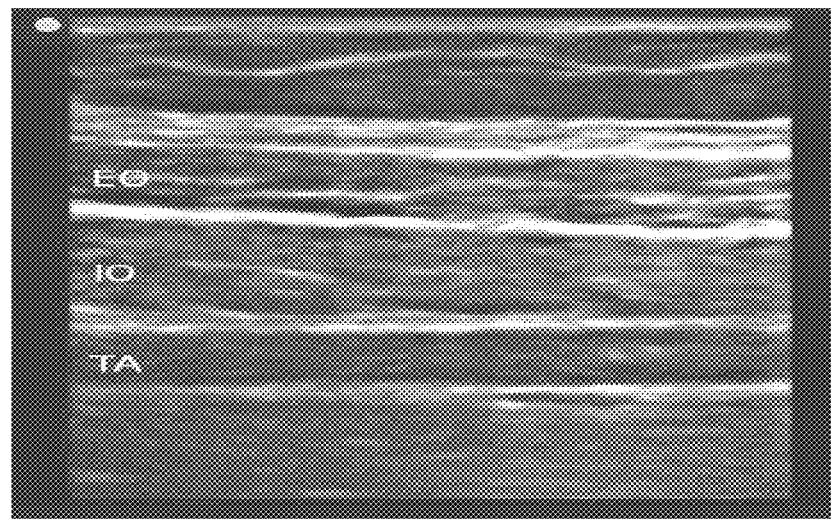
FIG. 2 is an ultrasound image of the muscular layers of the anterolateral abdominal wall.

The anatomy view of FIG. 1 is provided for an appreciation and understanding of a TAP block procedure. The anterior abdominal wall (including the skin, muscles, parietal peritoneum) is innervated by the anterior rami of the lower thoracic nerves and the first lumbar nerve. Terminal branches of these somatic nerves run through the lateral abdominal wall within a plane between the internal oblique and transverse abdominis muscles. This intermuscular plane is referred to as the transversus abdominis plane (TAP). Referring to FIG. 1, a TAP procedure is performed at the triangle of Petit, which is the area bounded posteriorly by the latissimus dorsi, anteriorly by the external oblique muscle, and inferiorly (base of the triangle) by the iliac crest. FIG. 2 is an ultrasound image of the external oblique (EO), internal oblique (IO), and transversus abdominis (TA) muscle layers. The procedure involves insertion of a needle from a direction transverse to the planes depicted in FIG. 2 through the EO, IO, and into the TAP plane. This plane has been shown to provide good postoperative analgesia for a variety of procedures.

FIGS. 3A through 3H depict various items and components that may be used by a practitioner to practice the TAP procedure described herein. It should be appreciated that the particular articles depicted in the figures and described herein are not limiting factors on practice of the present method, but are devices that have proven to be useful and preferred.

FIG. 3A depicts an embodiment of a needle 24 for use in the procedure, as discussed in greater detail below. The needle 24 may include a handle at the proximal (away from the patient) and a piercing tip at the distal end region 28. The needle 24 is particularly configured for delivery of a fluid through an injection site. A useful embodiment of a needle 24 is a Weiss epidural needle. In particular, the needle 24 may be a Weiss epidural needle supplied by Becton Dickinson (BD) having fixed wings 26 and a modified Tuohy point. The needle may be a five-inch, 18 gauge needle and is identified by the BD product number 405190. It should be appreciated, however, that other types of suitable epidural needles may also be utilized.

FIG. 3B depicts an extension set 40 for configuration with the proximal end of the needle 24. In a simple embodiment, the extension set 40 may be an extension tube 42 having any desired length, for example a thirty-inch extension tube. The extension set 40 may include any manner of additional components, such as a 90-degree adapter 44 that mates with the proximal end of the needle 24, with the tube 42 extending from the adapter 44 at a 90-degree angle relative to the axis of the needle 24. An embodiment of such an adapter is provided in a product commercially available from Braun and identified as the "Contiplex Tuohy Continuous Nerve Block Set" (product reference number 331691). A 30-inch extension set is available from Hospira (product reference number 3229-03).

FIG. 3C depicts an embodiment of a sheath 14 having a handle 16 at a proximal end thereof. An extension 18 extends perpendicularly from the handle 16 and terminates at a distal (towards the patient) end 22. The sheath 14 has a size and length such that the needle 24 extends through the sheath 14 with the distal end region 28 of the needle 24 extending distally from the end 22 of the sheath 14 when the components are configured together and inserted into the TAP region of the patient. The sheath 14 may be a generally semi-rigid or flexible member that has at least some ability to conform within the TAP region, particularly within the confines of the liquid pool generated in the TAP. A particularly useful sheath 14 is available from IFLO as a component of the 2.5 inch Soaker Catheter (product reference number PM 010).

The extension 18 of the sheath 14 is generally composed of a semi-rigid or flexible material, such as plastic, elastomeric, and the like. Such materials are, however, inherently nonechogenic. In this regard, it may be desired to render the extension portion 18 of the sheath 14 echogenic by, for example, forming the extension 18 with one or more echogenic elements integrated with the extension 18. These elements may be, for example, a metallic thread affixed to the outer surface of the extension portion 18 or embedded within the extension portion 18. Metallic flakes may be adhered or attached to the external surface of the extension portion 18, or impregnated within the extension portion 18.

In a particularly unique embodiment, the extension portion 18 of the sheath 14 may be rendered echogenic by simply perforating the extension portion 18 with a series of holes or other openings along the axial length thereof. These holes or openings essentially expose the needle 24 to ultrasonic imaging. Thus, portions or sections of the needle disposed within the extension portion 18 are visible in an ultrasonic imaging process, thereby essentially rendering the sheath echogenic. Referring to FIG. 3C, perforations 20 are depicted along the axial length of the extension portion 18 of the sheath 14.

FIG. 3D represents any manner of suitable catheter site dressing, which may be one or more Tegaderm™ products from 3M.

FIG. 3F depicts any manner of suitable syringe 46 that connects with the proximal end of the extension set 40 to deliver a local anesthetic or saline/anesthetic mixture through the extension set 40 and needle 24.

FIG. 3E depicts any number of vials 48 of local anesthetic, saline, or any other liquid that may be desired in performance of the TAP procedure.

FIG. 3G is meant to depict any manner of drape 52 that is uniquely configured for performance of the TAP procedure. For example, the drape 52 may have any manner of fenestration located within the drape 52 for access to the TAP procedure site. A suitable drape is provided by Arrow as a clear 24×36 inch fenestrated drape with a four-inch fenestration (with adhesive).

FIG. 3G depicts a continuous flow catheter 30 that is eventually deployed within the TAP region to provide a relatively continuous flow of a local anesthetic from a reservoir 36, through tubing 32, and eventually out through a delivery end 34. A suitable continuous flow catheter 30 is provided by IFLO as the 2.5 inch Soaker Catheter (product reference number PM010).

Figure 4:
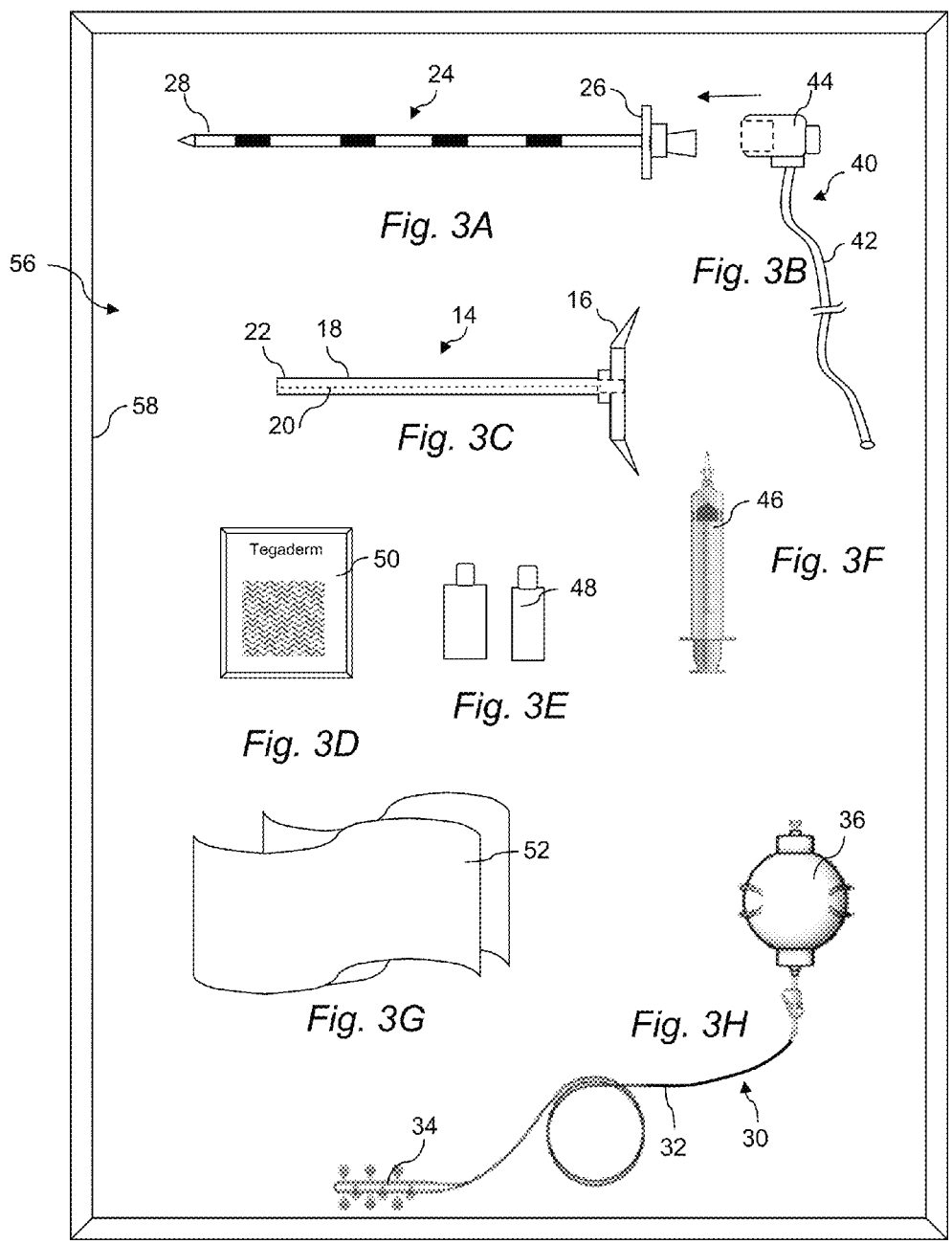
FIG. 4 depicts an assembly of various components of FIGS. 3A through 3H as a kit.

FIG. 4 is meant to depict a kit 56 that includes any manner of suitable container 58 in which is provided any combination of the components depicted in FIGS. 3A through 3H. The container 58 may be, for example, a suitable tray having a removable sealed covering in which the articles are contained. It should be appreciated that the kit 56 need not contain all of the articles depicted in FIGS. 3A through 3H. For example, an embodiment of the kit 56 may include the container 58 with a fluid delivery needle 24, extension set 40, sheath 14, and a continuous flow catheter 30, as discussed above. Other embodiments of a kit 56 may include additional items, such as the local anesthetic 48 (FIG. 3), syringe 46 (FIG. 3F), as well as any combination of drape 52 (FIG. 3G), catheter site dressing 50 (FIG. 3D), and so forth. The invention encompasses a kit 56 with any combination of the items of FIGS. 3A through 3H.

Figure 5A:
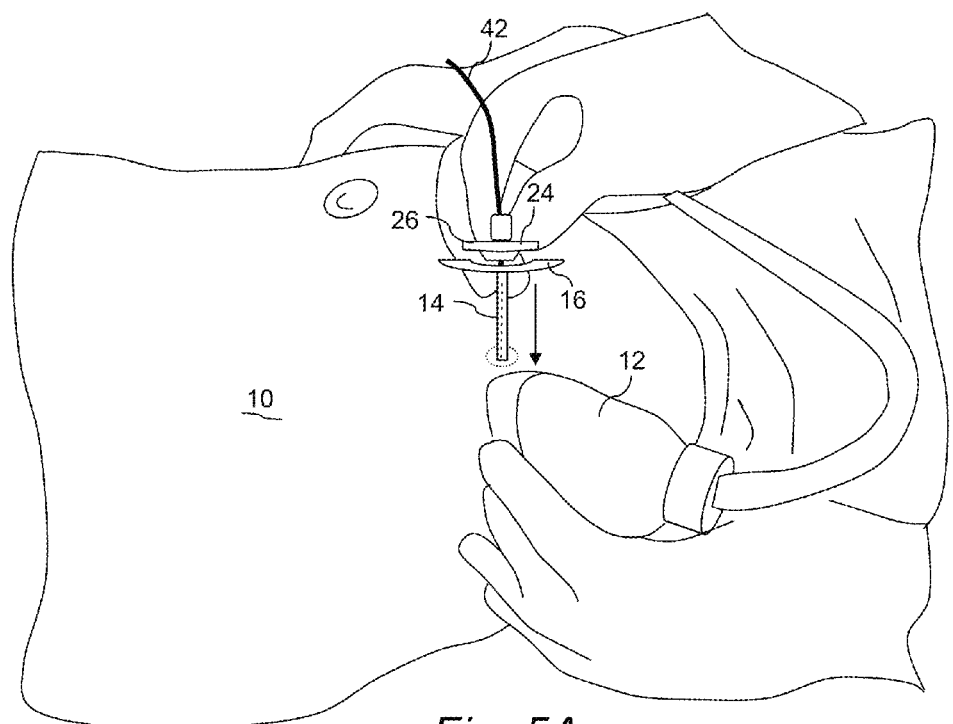
FIG. 5A is a perspective view of step of a step of an ultrasonically-guided TAP block procedure in accordance with aspects of the invention.
Figure 5B:
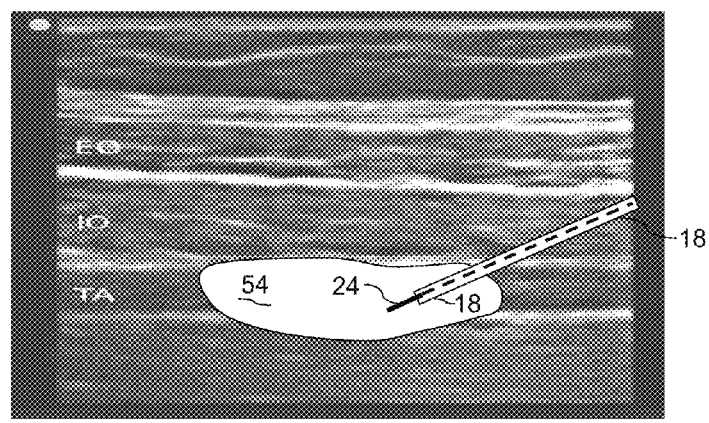
FIG. 5B is an ultrasonic image with a depiction of a needle and sheath within the TAP resulting from the step of FIG. 5A.

FIGS. 5A through 8B depict various procedural steps of a TAP block procedure in accordance with aspects of the invention. FIG. 5A depicts the abdominal region 10 of a patient that has been prepped for the TAP procedure. Any manner of suitable ultrasonic probe 12 is first used to identify and mark the external oblique (EO), internal oblique (IO), and transversus abdominis (TA). The epidural needle 24 has been inserted into the sheath 14 such that the distal end region of the needle 24 extends beyond the distal end of the sheath 14 (as depicted in FIG. 5A). While ultrasonically imaging the procedure site, the needle 24 and sheath 14 are advanced into the TAP and a liquid pool 54 (FIG. 5A) is created in the TAP by injecting a local anesthetic or saline/anesthetic combination through the needle 24 via a syringe and extension set 42, as discussed above. FIG. 5B depicts formation of the liquid pool 54 in the TAP. It can be appreciated from FIG. 5B that the distal end of the needle 24 is echogenic, and thus clearly distinguishable in an ultrasonic imaging procedure. The extension portion 18 of the sheath 14 has, in this particular embodiment, a series of perforations such that sections of the needle 24 within the extension section 18 are also visible in the ultrasonic imaging procedure. Thus, placement of the sheath 14 is also verified by referencing the position of the needle 24.

Figure 6A:
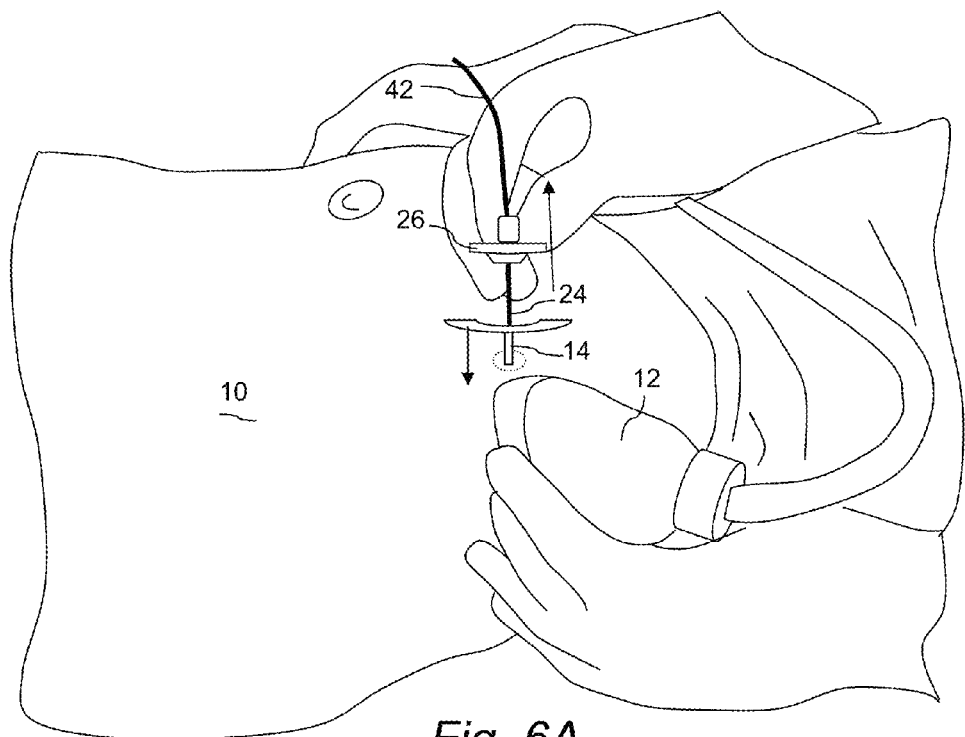
FIG. 6A is a perspective view of an additional step of the ultrasonically-guided TAP block procedure.
Figure 6B:
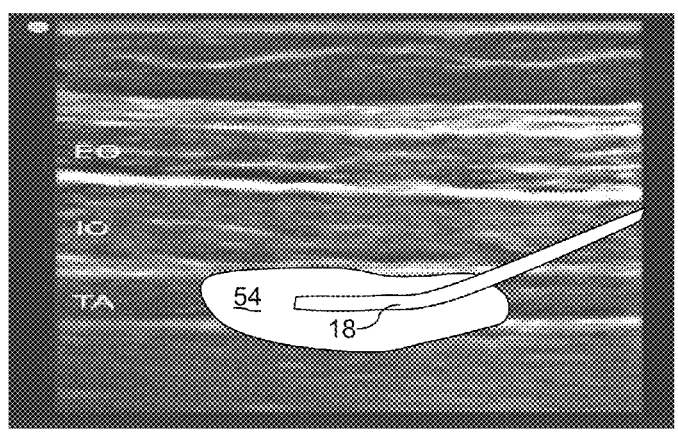
FIG. 6B is an ultrasonic image with a depiction of the sheath within the TAP resulting from the step of FIG. 6A.

FIGS. 6A and 6B depict a subsequent step wherein the needle 24 is removed from sheath 14 while maintaining the extension portion 18 of the sheath 14 within the liquid pool 54, as depicted by the arrows in FIG. 6A. The ultrasonic probe 12 may be useful for providing an image of removal of the needle 14. If the sheath 14 includes echogenic material, as discussed above, an ultrasonic imaging technique may also be used to verify that the sheath 14 is properly placed within the TAP, particularly within the liquid pool 54. With this step, it may also be desired to extend the sheath 14 further into the liquid pool 54, as depicted by the arrow in FIG. 6A, until a slight resistance is felt by the practitioner on the extension section 18.

Figure 7A:
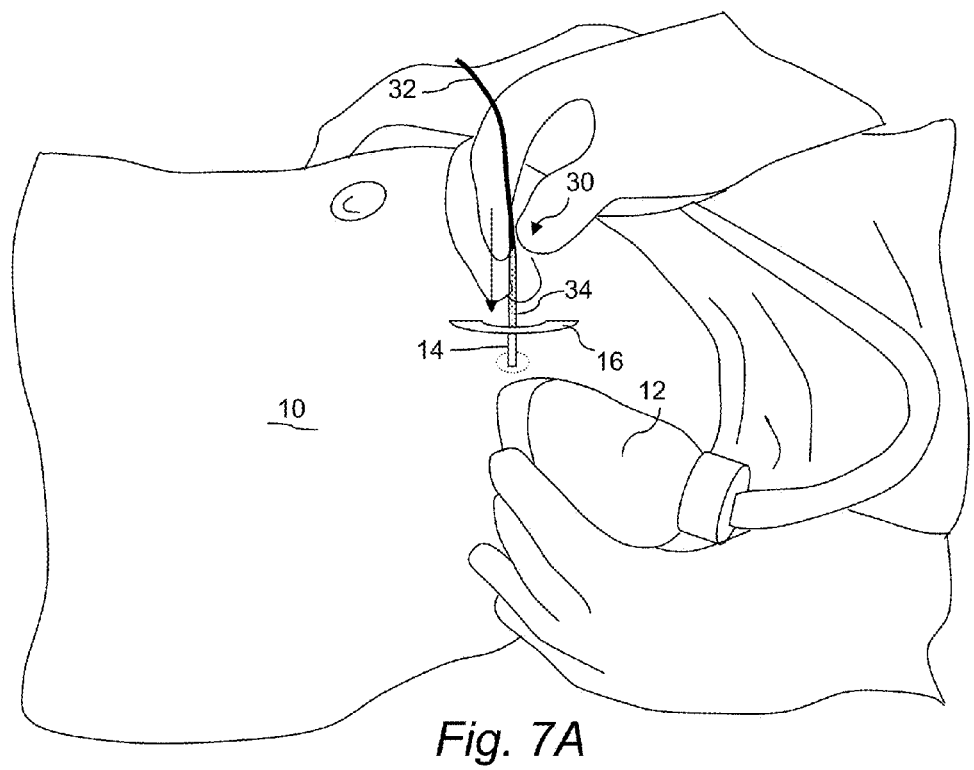
FIG. 7A is a perspective view of another step of the ultrasonically-guided TAP block procedure.
Figure 7B:
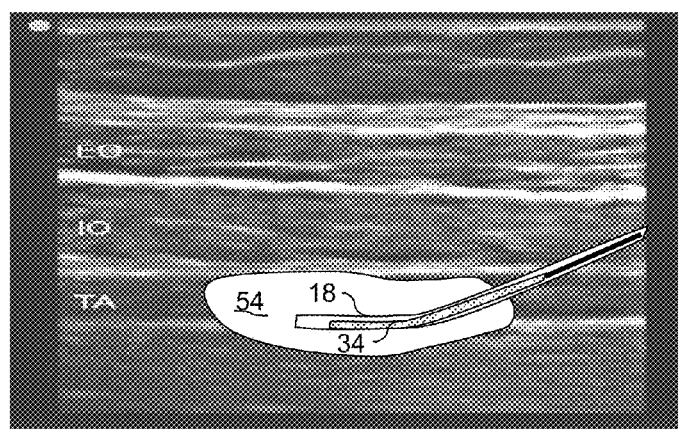
FIG. 7B is an ultrasonic image with a depiction of catheter and sheath within the TAP resulting form the step of FIG. 7A.

FIGS. 7A and 7B depict insertion of the catheter 30 through the sheath 14. In particular, the delivery end 34 of the catheter 30 is inserted through the sheath and resides within the extension portion 18 of the sheath 14 within the pool 54. During this procedure, back flow of the liquid from the pool 54 through the catheter 30 may be experienced, which is an indication of proper placement of the sheath 14 within the liquid pool 54.

Figure 8A:
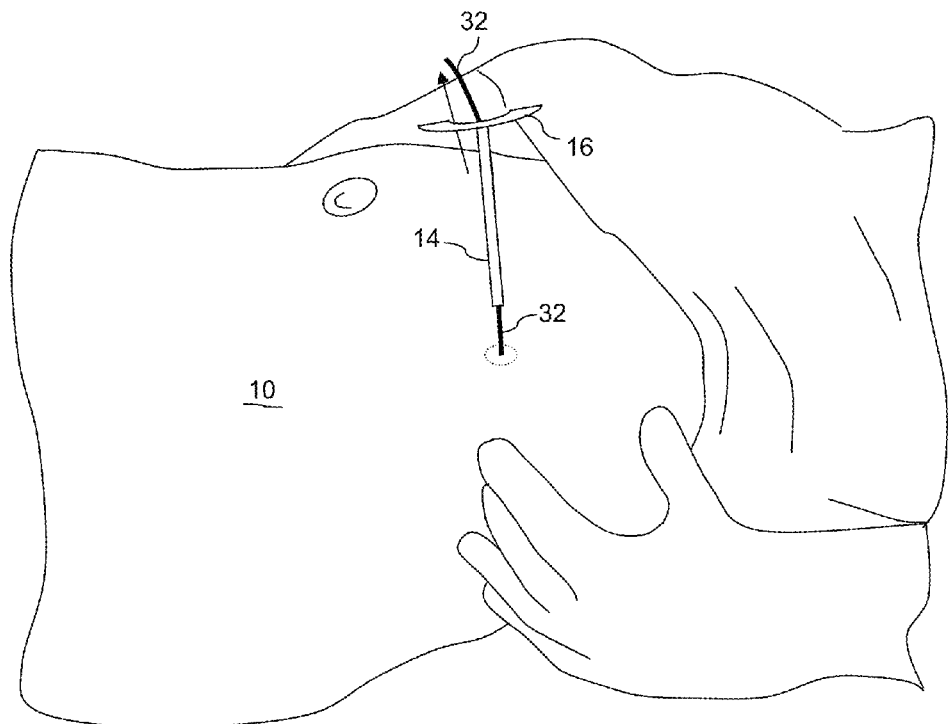
FIG. 8A is a perspective view of still another step of the ultrasonically-guided TAP block procedure.
Figure 8B:
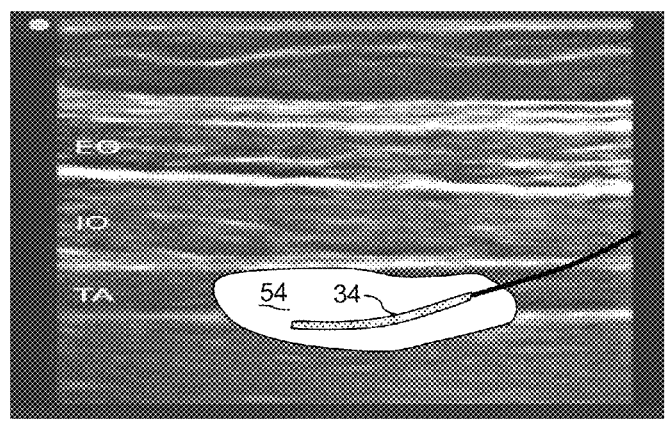
FIG. 8B is an ultrasonic image with a depiction of a continuous delivery catheter within the TAP.

Referring to FIGS. 8A and 8B, once the delivery end 34 of the catheter has been positioned within the pool 54, the sheath 14 is withdrawn from the TAP by being slid proximally over the catheter tubing 42 while maintaining the delivery end 34 of the catheter stationary within the liquid pool 54. The catheter site may then be dressed with any suitable dressing, such as the dressing 50 depicted in FIG. 3B. A reservoir of a local anesthetic is connected to the proximal end of the tubing 32 and configured for delivering a controlled flow rate of the local anesthetic over a prolonged defined time period. The catheter 30, including the reservoir 36, tubing 32, and the delivery end 34, may be configured as a single integral unit, or independent components that are subsequently connected together.

While the present invention has been described in connection with certain preferred embodiments it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed is:

1. A procedure for performing an ultrasound-guided transversus abdominis plane (TAP) procedure, comprising:

scanning a patient's abdomen with an ultrasound probe, and identifying and marking the external oblique, internal oblique, and TAP;

placing an introducer sheath over a fluid delivery needle such that the distal end of the needle extends beyond the distal end of the sheath, the needle having echogenic properties for ultrasound imaging;

ultrasonically guiding the needle and sheath into the TAP;

injecting a local anesthetic or saline/anesthetic combination through the needle and creating a liquid pool in the TAP;

removing the needle from the sheath while maintaining the sheath within the TAP and subsequently advancing a catheter through the sheath and into the pooled liquid in the TAP;

withdrawing the sheath while maintaining the catheter located within the TAP; and with the catheter located in the TAP, connecting the catheter to a local anesthetic source for providing a defined volume of anesthetic to the catheter site in the TAP at a controlled delivery rate.

2. The procedure as in claim 1, further comprising advancing the sheath distally away from the needle and further into the liquid pool in the TAP prior to or in conjunction with removing the needle from the sheath.

3. The procedure as in claim 1, wherein the needle is an epidural needle, and further comprising connecting the epidural needle to an extension tube, wherein the local anesthetic or saline/anesthetic combination is injected through the needle and tubing with a syringe.

4. The procedure as in claim 1, further comprising rendering the sheath echogenic so that placement of the sheath into the TAP is also visible with the ultrasonic probe.

5. The procedure as in claim 4, wherein the sheath is rendered echogenic by defining holes through the sheath along the axial length thereof.

6. The procedure as in claim 4, wherein the sheath is rendered echogenic by surface modification of sheath with echogenic material.

7. The procedure as in claim 1, wherein the catheter is connected to a reservoir of local anesthetic having a defined fill volume and flow rate.

* * * * *